(12) United States Patent
Thyagarajan et al.

(10) Patent No.: US 12,109,268 B2
(45) Date of Patent: **\*Oct. 8, 2024**

(54) NANOPARTICLE DELIVERY SYSTEM FOR TARGETED ANTI-OBESITY TREATMENT

(71) Applicant: UNIVERSITY OF WYOMING, Laramie, WY (US)

(72) Inventors: Baskaran Thyagarajan, Laramie, WY (US); Padmamalini Baskaran, Laramie, WY (US)

(73) Assignee: UNIVERSITY OF WYOMING, Laramie, WY (US)

( \* ) Notice: Subject to any disclaimer, the term of this patent is extended or adjusted under 35 U.S.C. 154(b) by 403 days.

This patent is subject to a terminal disclaimer.

(21) Appl. No.: 17/384,958

(22) Filed: Jul. 26, 2021

(65) Prior Publication Data

US 2021/0346499 A1 Nov. 11, 2021

Related U.S. Application Data

(60) Division of application No. 16/543,161, filed on Aug. 16, 2019, now Pat. No. 11,077,190, which is a
(Continued)

(51) Int. Cl.
*A61K 31/23* (2006.01)
*A61K 9/00* (2006.01)
(Continued)

(52) U.S. Cl.
CPC ............ *A61K 41/00* (2013.01); *A61K 9/0053* (2013.01); *A61K 9/5031* (2013.01); *A61K 9/5094* (2013.01); *A61K 9/5153* (2013.01);
*A61K 31/165* (2013.01); *A61K 31/23* (2013.01); *A61K 31/231* (2013.01); *A61K 31/357* (2013.01);
(Continued)

(58) Field of Classification Search
CPC .................................. A61K 41/00; A61K 9/51
See application file for complete search history.

(56) References Cited

U.S. PATENT DOCUMENTS 4,795,698 A \* 1/1989 Owen .................. A61K 9/5094
 435/7.92
6,235,788 B1 \* 5/2001 Terry ..................... A61K 31/16
 424/760

(Continued)

OTHER PUBLICATIONS

Y Jia et al. "Co-encapsulation of magnetic Fe3O4 nanoparticles and doxorubicin into biodegradable PLGA nanocarriers for intratumoral drug delivery." International Journal of Nanomedicine, vol. 7, 2012, pp. 1697-1708. (Year: 2012).\*

(Continued)

*Primary Examiner* — Isaac Shomer
(74) *Attorney, Agent, or Firm* — Patterson + Sheridan, LLP

(57) ABSTRACT

A magnetic nanoparticle including a TRPV1 agonist, as well as methods of preparation and use, are described herein. A magnetically responsive pharmaceutical can include a core region having a magnetic nanoparticle (MNPs) and a TRPV1 protein agonist. Further, an exterior coating comprising a polymer can be formed around the core region. The (Continued)

magnetically responsive pharmaceutical can be administered to a recipient and directed to a target region using an external magnetic field.

20 Claims, 4 Drawing Sheets

Related U.S. Application Data continuation of application No. 15/688,053, filed on Aug. 28, 2017, now Pat. No. 10,456,467, which is a continuation of application No. 15/132,488, filed on Apr. 19, 2016, now Pat. No. 9,782,481, which is a division of application No. 14/590,124, filed on Jan. 6, 2015, now Pat. No. 9,320,749.

(60) Provisional application No. 61/924,026, filed on Jan. 6, 2014.

(51) Int. Cl.
| | |
|---|---|
| A61K 9/50 | (2006.01) |
| A61K 9/51 | (2006.01) |
| A61K 31/165 | (2006.01) |
| A61K 31/231 | (2006.01) |
| A61K 31/357 | (2006.01) |
| A61K 31/7034 | (2006.01) |
| A61K 41/00 | (2020.01) |
| A61K 47/69 | (2017.01) |
| A61K 47/02 | (2006.01) |

(52) U.S. Cl.
CPC ...... *A61K 31/7034* (2013.01); *A61K 41/0052* (2013.01); *A61K 47/6941* (2017.08); *A61K 9/0019* (2013.01); *A61K 47/02* (2013.01); *Y10S 977/773* (2013.01); *Y10S 977/906* (2013.01)

(56) References Cited

U.S. PATENT DOCUMENTS

| | | | |
|---|---|---|---|
| 9,320,749 B2 | 4/2016 | Thyagarajan et al. | |
| 9,782,481 B2 | 10/2017 | Thyagarajan et al. | |
| 10,456,467 B2 * | 10/2019 | Thyagarajan | A61K 31/231 |
| 11,077,190 B2 * | 8/2021 | Thyagarajan | A61K 41/0052 |
| 2001/0051184 A1 * | 12/2001 | Heng | A61K 9/0014 |
| | | | 424/678 |
| 2004/0156852 A1 | 8/2004 | Daum et al. | |
| 2005/0090557 A1 | 4/2005 | Muhammad et al. | |
| 2005/0090732 A1 | 4/2005 | Ivkov et al. | |
| 2005/0271745 A1 * | 12/2005 | Gruettner | A61K 47/6929 |
| | | | 424/646 |
| 2008/0187595 A1 | 8/2008 | Jordan et al. | |
| 2009/0317408 A1 | 12/2009 | Ivkov et al. | |
| 2010/0047180 A1 | 2/2010 | Zeng et al. | |
| 2011/0105825 A1 | 5/2011 | Nayfach-Battilana | |
| 2012/0265001 A1 | 10/2012 | Asmatulu et al. | |
| 2016/0067338 A1 | 3/2016 | Jordan | |

OTHER PUBLICATIONS

Marco Lattuada and T. Alan Hatton. "Functionalization of Monodisperse Magnetic Nanoparticles." Langmuir, vol. 23, 2007, pp. 2158-2168. (Year: 2007).*

NK Verma et al. "Magnetic core-shell nanoparticles for drug delivery by nebulization." Journal of Nanobiotechnology, vol. 11:1, 2013, pp. 1-12. (Year: 2013).*

Y Jia et al. "Co-encapsulation of magnetic Fe3O4 nanoparticles and doxorubicin into biodegradable PLGA nanocarriers for intratumoral drug delivery." International Journal of Nanomedicine, vol. 7, 2012, pp. 1697-1708. (Year: 2012).*

A Abushrida. "Formulation of novel polymer coated iron oxide nanoparticles." PhD thesis, University of Nottingham. 2012. pp. i-xxv, 1-268, and two initial pages for 295 printed sheets.

A Akbarzadeh, M Samiei, S Davaran. "Magnetic nanoparticles: preparation, physical properties, and applications in biomedicine." Nanoscale Research Letters, vol. 7:144, 2012, pp. 1-13. (Year: 2012).

Aexander Bartell, et al, Adipose tissue browning and metabolic health, Nature Reviews Endocrinology. 10.1 (Jan. 2014), 15 pp.

Allessandro Peschechera, et al, "Browning" of adipose tissue—regulation and therapeutic perspectives, Arch Physiol; Biochem, 2013; 119(4): pp. 151-160.

Andrew J. Whittle, et al, BMP8B Increases Brown Adipose Tissue Thermogenesis through Both Central and; Peripheral Actions, Cell 149, May 11, 2012, pp. 871-885.

Arianne L. Motter, et al., TRPV1-null mice are protected from diet-induced obesity, FEBS Lett. Jun. 25, 2008; 582(15); pp. 2257-2262.

Claudio J. Villanueva, et al, Adipose subtype-selective recruitment of TLE3 or Prdm16 by PPARy specifies lipid-storage; versus thermogenic gene programs, Cell Metab. Mar. 5, 2013; 17(3): pp. 423-435.

Daoyan Liu, et al., The Role of Transient Receptor Potential Channels in Metabolic Syndrome, Hypertens Res vol. 31,; No. 11 (2008), 7 pp.

Derek C Molliver, et al., ASIC3, an acid-sensing ion channel, is expressed in metaboreceptive sensory neurons,; Molecular Pain Jan. 2005:35, 13 pp.

DL Cioffi. "The Skinny on TRPV1." Circulation Research, vol. 100, 2007, pp. 934-936.

Haruya Ohno, et al., PPAR agonists induce a white-to-brown fat conversion through stabilization of PRDM16 protein, Cell Metab. Mar. 7, 2012; 15(3): pp. 395-404.

Irina G. Shabalina, et al, UCP1 in Brite/Beige Adipose Tissue Mitochondria Is Functionally Thermogenic, Cell Reports; 5, Dec. 12, 2013, pp. 1196-1203.

J. Ren, Leptin and hyperleptinemia—from friend to foe for cardiovascular function, Journal of Endocrinology (2004); 181, pp. 1-10.

Jarek Maestu, Visfatin and Adiponectin Levels in Children: Relationships with Physical Activity and Metabolic; Parameters, Cytokines, Growth Mediators and Physical Activity in Children during Puberty. Med Sport Sci. Basel,; Karger, 2010, vol. 55, pp. 56-68.

Jerel P. Calzo, et al, Development of Muscularity and Weight Concerns in Heterosexual and Sexual Minority Males,; Health Psychol. Jan. 2013 32(1): pp. 42-51.

Ji-Hye Kang, et al., Dietary Capsaicin Reduces Obesity-induced Insulin Resistance and Hepatic Steatosis in Obese; Mice Fed a High-fat Diet, Obesity (2010) 18, pp. 780-787.

Kinyui Alice Lo, et al., Turning WAT into BAT: a review on regulators controlling the browning of white adipocytes,; Biosci. Rep. (2013) / 33, 9 pp.

Lei Cao, et al, While to brown fat phenotypic switch induced by genetic and environmental activation of a; hypothalamic-adipocyte axis, Cell Melab. Sep. 7, 2011; 14(3): pp. 324-338.

Li Qiang, et al., Brown Remodeling of White Adipose Tissue by SirT1-Dependent Deacetylation of Ppar?, Cell Aug. 3, 2012; 150(3): pp. 620-632.

LL Zhang et al. "Activation of Transient Receptor Potential Vanilloid Type-1 Channel Prevents Adipogenesis and Obesity." Circulation Research, vol. 100, 2007, pp. 1063-1070.

M Baskaran, B Thyagarajan. "Preparation and Evaluation of PLGA Coated Capsaicin Magnetic Nanoparticles for Target Siteu Specific Pain Therapeutics." http://www.cell.com/biophysj.pdf/S0006-3495(14)01908-0.pdf, (item 625-Pos) accessed on Jun. 6, 2017,published on Feb. 8, 2015, 1 printed page.

Maarten J. Vosselman, et al., Energy dissipation in brown adipose tissue: From mice to men, Molecular and Cellular; Endocrinology 379 (2013) pp. 43-50.

Manuela Tramonlana, et al., Excitatory and inhibitory urinary bladder reflexes induced by stimulation of cervicovaginal capsaicin-sensitive sensory fibers in rats, Naunyn-Schmiedeberg's Arch Pharmacol (2009) 379: pp. 107-114.

(56) References Cited

OTHER PUBLICATIONS

Maria Servera, et al., Expression of "brown-in-white" adipocyte biomarkers shows gender differences and the influence; of early dietary exposure, Genes Nutr (2014) 9:372, 9 pp.
Marica Bordicchia, et al., Cardiac nalriurelic peptides act via p38 MAPK to induce the brown fat lhermogenic program; n mouse and human adipocytes, The Journal of Clinical Investigation, Mar. 2012, vol. 122, No. 3, 15 pp.
Mark L. Hatzenbuehler, et al, Stigma as a Fundamental Cause of Population Health Inequalities, American Journal of; Public Health, May 2013, vol. 103, No. 5, 9 pp.
Masaki Futamura, et al., Differential effects of topically applied formalin and aromatic compounds on; neurogenicmediated; microvascular leakage in rat skin, Toxicology 255 (2009) pp. 100-106.
Matthijs K.C. Hesselink, et al., Human Uncoupling Protein-3 and Obesity: An Update, Obesity Research, vol. 11, No. 12, Dec. 2003, 15 pp.
Meritxell Rosell, et al, Brown and white adipose tissues: intrinsic differences in gene expression and response to cold; exposure in mice, Am J Physiol Endocrinol Metab 306: 2014, pp. E945-E964.
Muralidharan Anbalagan, et al, Post-translational modifications of nuclear receptors and human disease, Nuclear; Receptor Signaling (2012) 10, e001, 13 pp.
Nathan Robbins, et al., Targeting TRPV1 and TRPV2 for potential therapeutic interventions in cardiovascular disease,; Translational Research, Jun. 2013, 8 pp.
Nichola J. Marshall, et al., A Role for TRPV1 in Influencing the Onset of Cardiovascular Disease in Obesity,; Hypertension, Jan. 2013, 24 pp.
NK Verma, K Crosbie-Staunton, A Satti, S Gallagher, KB Ryan, T Toddy, C McAtamney, R Macloughlin, P. Galvin, CS Burke, Y v Volkov, YK Gun'ko. "Magnetic core-shell nanoparticles for drug delivery by nebulization." Journal of anobiotechnology, vol. 11:1, 2013, pp. 1-12.
Notice of Allowance for U.S. Appl. No. 15/132,488 dated Jun. 15, 2017.
Office Action for U.S. Appl. No. 14/590,124 dated Aug. 3, 2015.
Office Action for U.S. Appl. No. 15/132,488 dated Mar. 13, 2017.
Olivier van Beekum, et al, Posttranslational Modifications of PPAR-y: Fine-tuning the Metabolic Master Regulator,; Obesity (2009) 17, pp. 213-219.
Patrick Seale, et al, PRDM16 controls a brown fat/skeletal muscle switch, Nature, vol. 454, Aug. 21, 2008, 8 pp.
Paul Cohen, et al, Ablation of PRDM16 and Beige Adipose Causes Metabolic Dysfunction and a Subcutaneous to; Visceral Fat Switch, Cell Jan. 16, 2014; 156(0), pp. 304-316.
Pengpeng Bi, et al., Inhibition of Notch signaling promotes browning of while adipose tissue and ameliorates obesity,; Nature Medicine, Aug. 2014, vol. 20, No. 8, 10 pp.
Qi Yu, et al., Expression of TRPV1 in rabbits and consuming hot pepper affects its body weight, Mol Biol Rep (2012); 39: pp. 7583-7589.
Rector Arya, et al., Linkage of high-density lipoprotein-cholesterol concentrations to a locus on chromosome 9p in;; Mexican Americans, Nature Genetics, Jan. 2002, vol. 30, 4 pp.
S Chanda, M Bashir, S Babbar, A Kognanti, K Bley, "In Vitro Hepatic and Skin Metabolism of Capsaicin." Drug Metabolism and Disposition, vol. 36, No. 4, 2008, pp. 670-675. (Year: 2008).
Shusuke Yagi, et al., Association of lower limb muscle mass and energy expenditure with visceral fat mass in healthy; men, Diabetology & Metabolic Syndrome 2014, 6:27, 5 pp.
Subal Turdi, et al., Deficiency in AMP-activated protein kinase exaggerates high fat diet-induced cardiac; hypertrophy; and contractile dysfunction, Journal of Molecular and Cellular Cardiology 50 (2011) pp. 712-722.
Tahn, JH Kim, H-M Yang, JW Lee, J-D Kim, "Formation Pathways of Magnetic Nanoparticles by Coprecipitation Method." The Journal of Physical Chemistry C, vol. 116, 2012, pp. 6069-6076. (Year: 2012).
Takeshi Yoneshiro, et al., Transient receptor potential activated brown fat thermogenesis as a target of food; ngredients for obesity management, Curr Opin Clin Nutr Metab Care 2013, 16: pp. 625-631.
Xiaodan Lu, et al., Resistance to Obesity by Repression of VEGF Gene Expression through Induction of Brown-Like; Adipocyte Differentiation, Endocrinology, Jul. 2012, 153(7): pp. 3123-3132.
Xiaoting Jiang, et al., Inhibition of HDAC3 promotes ligand-independent PPAR activation by protein acetylation, J Mol; Endocrinol. Oct. 2014, 53(2): pp. 191-200.
Xingxing Kong, et al., IRF4 Is a Key Thermogenic Transcriptional Partner of PGC-1a, Cell 158, Jul. 3, 2014, pp. 69-83.

\* cited by examiner

NANOPARTICLE DELIVERY SYSTEM FOR TARGETED ANTI-OBESITY TREATMENT

CROSS-REFERENCE TO RELATED APPLICATIONS

This application is a divisional of U.S. patent application Ser. No. 16/543,161, filed Aug. 16, 2019, which is a continuation of U.S. patent application Ser. No. 15/688,053, filed Aug. 28, 2017, which is a continuation of U.S. patent application Ser. No. 15/132,488, filed Apr. 19, 2016, which is a divisional of U.S. patent application Ser. No. 14/590,124, filed Jan. 6, 2015, which claims benefit of U.S. Provisional Patent Application No. 61/924,026 filed Jan. 6, 2014, all of which are herein incorporated by reference in their entirety.

GOVERNMENT RIGHTS

This invention was made with government support under GM103432 awarded by the National Institute of General Medical Sciences, a division of the National Institutes of Health (NIH). The government has certain rights in the invention.

BACKGROUND

Field

Embodiments of the present disclosure generally relate to nanoparticles for controlled drug delivery and methods of using the same.

Description of the Related Art

Obesity is a medical condition in which excess body fat has accumulated to an extent that it may have a negative effect on health, leading to reduced life expectancy and/or increased health problems. In Western countries, people are considered obese when their body mass index (BMI), a measurement obtained by dividing a person's weight by the square of the person's height, exceeds 30 kg/m$^2$, with the range 25-30 kg/m$^2$ defined as overweight. Obesity increases the likelihood of various diseases, particularly heart disease, type 2 diabetes, obstructive sleep apnea, certain types of cancer, and osteoarthritis. Obesity is most commonly caused by a combination of excessive calorie intake, lack of physical activity, and genetic susceptibility to obesity, although a few cases are caused primarily by genes, endocrine disorders, medications, or psychiatric illness.

Dieting and exercise are the primary treatments for obesity. Diet quality can be improved by reducing the consumption of energy-dense foods, such as those high in fat and sugars, and by increasing the intake of dietary fiber. With a suitable diet, anti-obesity drugs may be taken to reduce appetite or decrease fat absorption. However, diet and exercise may be insufficient to achieve a desired BMI, with preexisting metabolic conditions and patient non-compliance being the primary reasons for failure. In some cases, medical intervention may be appropriate. Medical intervention can include a gastric balloon, a gastric band, or surgery may be performed to reduce stomach volume and/or bowel length, leading to feeling full earlier and a reduced ability to absorb nutrients from food. However, medical interventions can fail for similar reasons as described above. As well, medical interventions carry the inherent risks of adverse events related to all surgeries, such as sepsis or necrosis of the affected regions.

Non-invasive approaches have also been considered. Specifically, pharmacological approaches to anti-obesity (e.g., anti-obesity drugs) carry promise for future treatment. Drugs, such as capsaicin, have been shown to increase metabolism and reduce obesity in mouse models. As is the case with many drugs, capsaicin requires relatively large and sustained doses to achieve the anti-obesity effect. Further, capsaicin is not known to localize to a specific region or cell type, thus increasing the quantity of the drug needed to achieve the anti-obesity effect. The mechanism by which capsaicin prevents weight gain was unknown, further complicating localization. Finally, the prolonged use of pure capsaicin has a variety of side effects, which may limit patient compliance including gastrointestinal discomfort, esophageal irritation, and others related to the burning sensation created by capsaicin. There is currently no therapeutic drug available to decrease abnormal body weight gain.

Accordingly, what is needed in the art is an anti-obesity formulation which can be targeted to specific tissue regions and deliver a sustained release.

SUMMARY

Embodiments disclosed herein include a targeted anti-obesity drug and methods of using the same.

In one embodiment, a magnetically responsive pharmaceutical can include a core region having a magnetic nanoparticle (MNPs); a TRPV1 protein agonist; and an exterior coating comprising a polymer.

In another embodiment, an oral pharmaceutical composition in solid unit dosage form suitable for swallowing can include from about 1% to about 100% of a magnetically responsive pharmaceutical, the magnetically responsive pharmaceutical comprising: a core region having a magnetic nanoparticle (MNPs); a TRPV1 protein agonist; and an exterior coating comprising a polymer; and from about 0% to about 99% pharmaceutically-acceptable excipients.

In another embodiment, a method for making a magnetically responsive pharmaceutical can include precipitating ferromagnetic metal salts in the presence of ammonium hydroxide to obtain magnetic nanoparticles (MNPs); depositing a TRPV1 protein agonist in or around the MNPs; and coating the MNPs and the TRPV1 protein agonist with a polymer.

In another embodiment, a method of using a magnetically responsive pharmaceutical can include administering a magnetically responsive pharmaceutical to a recipient, the magnetically responsive pharmaceutical comprising a plurality of magnetic nanoparticles; a TRPV1 protein agonist; and a polymer, wherein the magnetically responsive pharmaceutical is absorbed and distributed over a period of time to at least a target region of the recipient; and providing a magnetic field to the target region, the magnetic field localizing at least a portion of the magnetically responsive pharmaceutical to the target region, the magnetically responsive pharmaceutical releasing the TRPV1 protein agonist; and maintaining the magnetic field until a desired dose of the TRPV1 protein agonist is delivered over a desired period of time in the target region.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, wherever possible, to designate identical elements that are common to the Figures. Additionally, elements of one embodiment may be advantageously adapted for utilization in other embodiments described herein.

DETAILED DESCRIPTION

Embodiments disclosed herein include a targeted anti-obesity drug and methods of using the same. We have found that the TRPV1 protein is active in the control of obesity. Embodiments described herein include a pharmaceutical composition having magnetic nanoparticles (MNPs) co-precipitated, intercalated or coated with a TRPV1 protein agonist, such as capsaicin. The transient receptor potential vanilloid 1 channel protein (TRPV1 protein) is a protein that, in humans, is encoded by the TRPV1 gene. This protein is a member of the TRPV group of transient receptor potential family of ion channels. Adipose tissue, epididymal, inguinal and brown fat pads express TRPV1 channel proteins endogenously and high fat diet-feeding suppresses TRPV1 expression in these tissues. The function of the TRPV1 protein is detection and regulation of body temperature (e.g., non-shivering thermogenesis). In addition, the TRPV1 protein provides sensation of scalding heat and pain.

TRPV1 protein agonists, such as capsaicin, are a promising group of compounds for the treatment of obesity. Capsaicin (CAP) has been shown to inhibit high fat diet-induced weight gain in mouse model systems. Further, in the absence of the TRPV1 protein in adipose tissue, CAP does not inhibit high fat diet-induced weight gain. By presenting the TRPV1 protein agonist as part of a targeted delivery system, the concentration of TRPV1 protein agonist available can be sustained over a long period of time while localizing the distribution of the drug. By controlling both distribution and available concentration to the target region, side effects can be mitigated while allowing for higher sustained concentrations of the TRPV1 protein agonist at the target region. Embodiments are more clearly described with reference to the figures below.

Figure 1A:
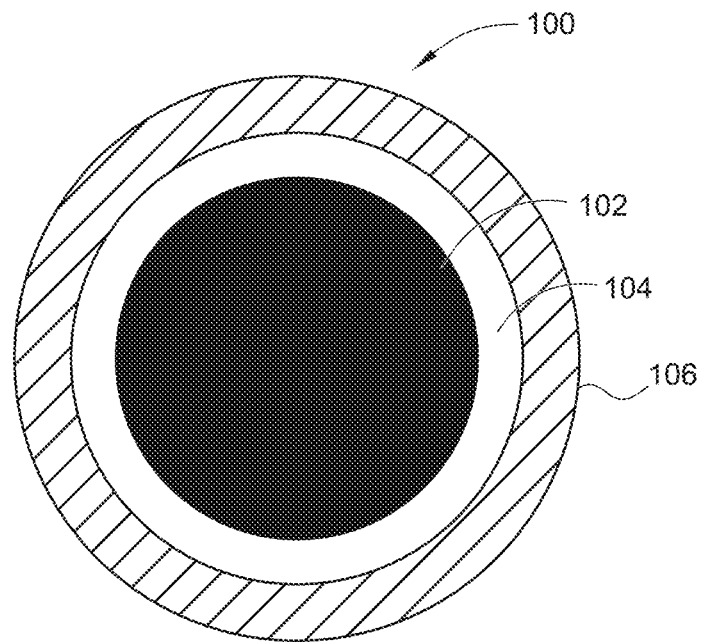
FIGS. 1A and 1B depict a cut away view of a magnetically responsive pharmaceutical, according to embodiments described herein.
Figure 1B:
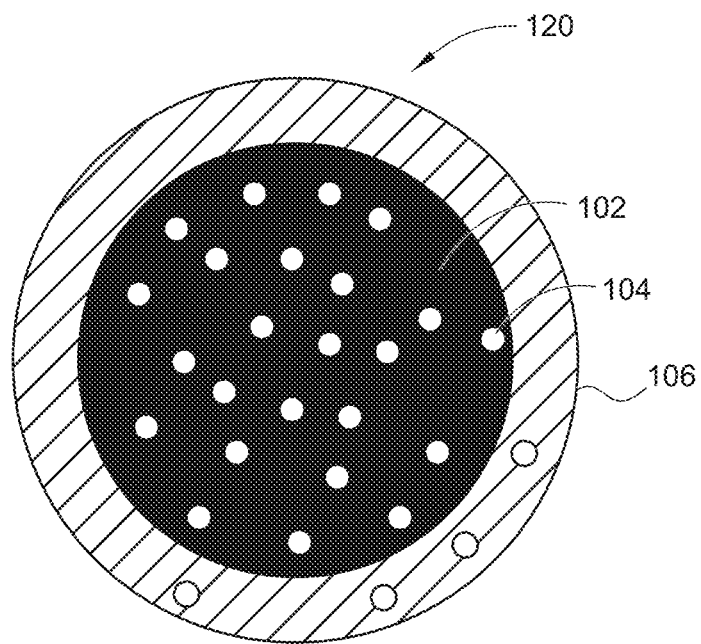

FIGS. 1A and 1B depict a cut away view of a magnetically responsive pharmaceutical 100 and a magnetically responsive pharmaceutical 120, according to embodiments described herein. FIG. 1A depicts the magnetically responsive pharmaceutical 100 having a magnetic nanoparticle (MNPs) 102 with a TRPV1 protein agonist 104 layer formed around it. A polymer 106 coats both the MNPs 102 and the TRPV1 protein agonist 104. FIG. 1B depicts the magnetically responsive pharmaceutical 120 with a magnetic nanoparticle (MNPs) 102 interspersed with a TRPV1 protein agonist 104. The polymer 106 coats both the MNPs 102 and the TRPV1 protein agonist 104.

As used herein, the MNPs 102 is a class of nanoparticle which can be manipulated using a magnetic field. MNPs 102 may include ferromagnetic materials, including but not limited to iron, nickel, cobalt or combinations thereof, as well as oxides thereof. In one embodiment, the MNPs 102 comprises an iron-based nanoparticle, such as an iron oxide nanoparticle. In another embodiment, the iron oxide nanoparticle comprises $Fe^{3+}$ and/or $Fe^{2+}$ ions. In embodiments which use a combination of $Fe^{3+}$ and $Fe^{2+}$ ions, the molar ratio can be between about 3:1 and about 1:1 $Fe^{3+}$ to $Fe^{2+}$ ions, such as about 2:1 of $Fe^{3+}$ to $Fe^{2+}$ ions. Metal salts which can be used for creating the MNPs 102 include but are not limited to iron, nickel or cobalt-based salts or combinations thereof. Suitable iron salts include, but are not limited to, iron(II) sulfate, iron(II) nitrate, iron(II) chloride, iron(II) perchlorate, iron(III) sulfate, iron(III) nitrate, iron(III) chloride, iron(III) perchlorate, and mixtures thereof.

Methods for preparing the MNPs 102 are known in the art. Though described here in reference to a single MNP 102 for clarity, it is understood that many MNPs 102 are produced in a single cycle using the embodiments described herein. MNPs can be made by methods including but not limited to co-precipitation, thermal decomposition, microemulsion, flame spray synthesis, and others. In one embodiment, ferric chloride and ferrous chloride are dissolved in degassed deionized water. Ammonium hydroxide is then added to the mixture. The flask is then heated to above 60 degrees Celsius, such as about 75 degrees Celsius followed by cooling to at or below room temperature, such as about 22 degrees Celsius. Optionally, the TRPV1 protein agonist 104 can be added to the mixture prior to heating and cooling such that the TRPV1 protein agonist 104 co-precipitates with the MNPs 102. The MNPs 102 are then magnetically filtered and washed with deionized water and neutralized with NaOH. In another embodiment, magnetic nanoparticles can be prepared. The desired quantity of TRPV1 agonist (capsaicin) can then be dissolved in suitable solvent (ethanol) and added to the nanoparticles. Solvent evaporation of ethanol causes deposition of capsaicin on the magnetic nanoparticles. These TRPV1 agonist adsorbed magnetic nanoparticles can then be coated with 1% PLGA and dissolved in a suitable solvent, such as dichloromethane. The solvent can then be evaporated, such as through the use of a rotary evaporator.

In one embodiment, the MNPs 102 are between about 5 nm and about 30 nm in diameter. In other embodiments, the MNPs 102 are between about 5 nm and about 25 nm, about 5 nm and about 20 nm, about 2 nm and about 15 nm, about 5 nm and about 10 nm, about 7.5 nm and about 30 nm, about 7.5 nm and about 25 nm, about 7.5 nm and about 20 nm, about 7.5 nm and about 15 nm, about 10 nm and about 30 nm, about 10 nm and about 25 nm, about 10 nm and about 20 nm, about 10 nm and about 15 nm, about 15 nm and about 30 nm, about 15 nm and about 25 nm, about 15 nm and about 20 nm, about 20 nm and about 30 nm, or about 20 nm and about 25 nm in diameter.

In another embodiment, the filtered MNPs 102 can be suspended in degassed and deionized water. The suspension of the MNPs 102 in water can then be heated to a temperature of between 40 degrees Celsius and 100 degrees Celsius for at least 2 minutes. In one example, the suspension can be heated to 50° C. in a closed vial for 5 min.

The TRPV1 protein agonist 104, such as capsaicin (CAP), can then be added to the suspension. The TRPV1 protein agonist 104 can be at an initial concentration, which is limited only by the solubility of the agonist in the solvent. Solvents include organic solvents, such as ethanol. The solvent may further include aqueous solvents, such as water, phosphate buffered saline (PBS), or other suitable solvent materials. Though described with reference to CAP, it is understood that the TRPV1 protein agonist can be any available TRPV1 protein agonist, including dihydrocapsiate, capsaicin, civamide, endovanilloids, resiniferatoxin, N-Vanillylnonanamide, capsiate, Capsaicin β-D-Glucopyranoside combinations thereof or metabolic products thereof. In embodiments where CAP is the TRPV1 protein agonist 104, CAP can be at an initial concentration of between about 100 micromolar (μM) and about 1 millimolar (mM). In the embodiments described above, the final concentration of CAP when added to the suspension is between about 1 μM and about 100 μM.

Optionally, the aqueous phase may be decanted and the combination of the MNPs 102 and the TRPV1 protein agonist 104 may be dried in a vacuum oven. In embodiments depicted in FIG. 1A, where the TRPV1 protein agonist 104 is added after the precipitation of the MNPs 102, the TRPV1 protein agonist 104 will predominately form a coating over the MNPs 102. In embodiments depicted in FIG. 1B, where the TRPV1 protein agonist 104 is co-precipitated with the MNPs 102, the TRPV1 protein agonist 104 is interspersed into the MNPs 102.

The polymer 106 may then be added to the suspension. The polymer 106 may be any polymer that is biocompatible when used in pharmaceuticals. The polymer 106 may be a biodegradable polymer. In one embodiment, the polymer comprises poly(lactic-co-glycolic acid) (PLGA), Polylactic acid (PLA), Polyglycolic acid (PGA), poly-D-lactic acid (PDLA), PLGA-dimethacrylate, fluorescent PLGA polymers, Eudragit RL, Eudragit RS, Ethyl cellulose, cellulose derivatives, or combinations thereof. In another embodiment, the polymer is PLGA. Depending on the ratio of lactide to glycolide used for the polymerization, different forms of PLGA can be obtained. The forms of PLGA are usually identified in regard to the molar ratio of the monomers used (e.g., PLGA 75:25 identifies a copolymer whose composition is 75% lactic acid and 25% glycolic acid). The crystallinity of PLGAs can vary from fully amorphous to fully crystalline depending on block structure and molar ratio. PLGAs typically show a glass transition temperature in the range of about 40 degrees Celsius to about 60 degrees Celsius. PLGA can be dissolved by a wide range of solvents, depending on composition. Higher lactide polymers can be dissolved using chlorinated solvents whereas higher glycolide materials will require the use of fluorinated solvents such as hexafluoroisopropanol (HFIP).

The polymer 106 acts to slow the release of the TRPV1 protein agonist 104. The TRPV1 protein agonist 104 is released into the local environment at a steady and sustained rate. Further, the polymer 106 acts to minimize agglomeration of the MNPs 102, leading to better dispersion of the TRPV1 protein agonist 104 throughout the target region.

PLGA degrades by hydrolysis of its ester linkages in the presence of water. It has been shown that the time required for degradation of PLGA is related to the monomers' ratio used in production, where the higher the content of glycolide units, the lower the time required for degradation as compared to predominantly lactide materials. In embodiments where the polymer 106 is PLGA, the PLGA may be dissolved in a miscibility agent, such as methylene chloride, prior to adding to the suspension. The aqueous phase of the suspension, which includes the magnetically responsive pharmaceutical 100 and/or the magnetically responsive pharmaceutical 120, can then be decanted. The magnetically responsive pharmaceutical 100 and/or the magnetically responsive pharmaceutical 120 can then be dried, such as in a vacuum oven.

Surface coating of the MNPs with polymer layers not only coat the MNPs, but also attenuate their cluster behavior in aqueous media, resulting in smaller MNPs cluster sizes compared to previous MNPs. Reduced cluster size and behavior makes the MNPs more suitable for biomedical applications. Thus, in another embodiment, the MNPs comprises an MNPs cluster of 200 nm or less in diameter, such as between about 50 nm and about 200 nm in diameter. In various embodiments, the MNPs clusters are between about 75 nm and about 200 nm; about 90 nm and about 200 nm; about 100 nm and about 200 nm; about 75 nm and about 175 nm; about 90 nm and about 175 nm; about 100 nm and about 175 nm; about 75 nm and about 150 nm; about 90 nm and about 150 nm; about 100 nm and about 150 nm; about 75 nm and about 125 nm; about 90 nm and about 125 nm; about 100 nm and about 125 nm; about 75 nm and about 110 nm; about or 90 nm and about 110 nm in diameter.

Any suitable amount of polymer can be used that can result in MNPs, and clusters thereof, of a size suitable for an intended use. In various embodiments, the MNPs comprise a molar ratio of between about 1:40 to about 1:300 polymer: metal ion in the MNPs. In various further embodiments, the MNPs comprise a molar ratio of between about 1:40 to 1:250; 1:40 to 1:200; 1:40 to 1:150; 1:40 to 1:100; 1:40 to 1:80; 1:80 to 1:300; 1:100 to 1:300; 1:150 to 1:300; 1:200 to 1:300; or 1:250 to 1:300 polymer:metal ion in the MNPs. In a further embodiment, the MNPs comprise a molar ratio of between about 1:1 and 1:10 polymer:metal ion in the MNPs. In various further embodiments, the molar ratio is between about 1:2 to about 1:9; about 1:3 to about 1:8; about 1:4 to about 1:7; about 1:5 to about 1:6; or is about 1:1, about 1:2, about 1:3, about 1:4, about 1:5, about 1:6, about 1:7, about 1:8, about 1:9, or about 1:10.

Figure 2:
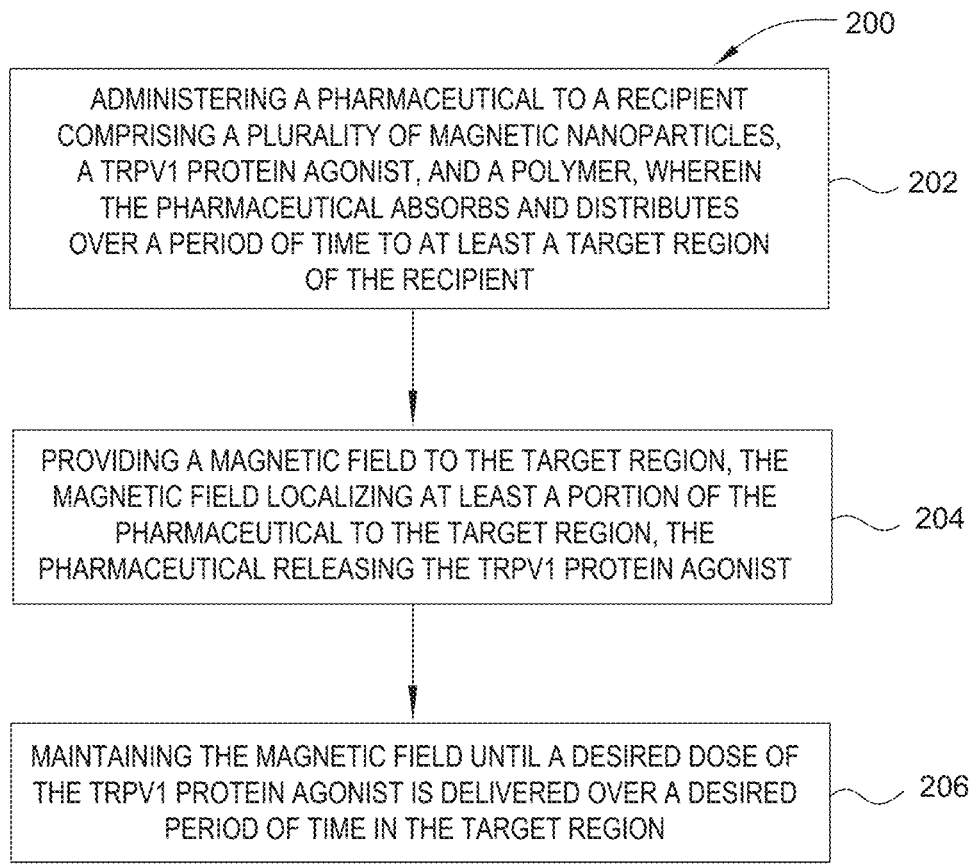
FIG. 2 is a flow diagram of a method of using the magnetically responsive pharmaceutical described in embodiments herein.

FIG. 2 is a block diagram of a method 200 of using the magnetically responsive pharmaceutical described in embodiments herein. The method 200 can include administering a magnetically responsive pharmaceutical to a recipient, wherein the magnetically responsive pharmaceutical absorbs and distributes over a period of time to at least a target region of the recipient, at 202; providing a magnetic field to the target region, the magnetic field localizing at least a portion of the magnetically responsive pharmaceutical to the target region, the magnetically responsive pharmaceutical releasing the TRPV1 protein agonist, at 204; and maintaining the magnetic field until a desired dose of the TRPV1 protein agonist is delivered over a desired period of time in the target region, at 206.

The method begins by administering the magnetically responsive pharmaceutical to a recipient, at 202. In all of the embodiments described herein, the magnetically responsive pharmaceutical may be administered orally, parenterally, topically, by inhalation or spray or rectally (depending on the location and availability of the tissue region) in dosage unit formulations containing conventional non-toxic pharmaceutically acceptable carriers, adjuvants and vehicles. The term parenteral as used herein includes percutaneous, subcutaneous, intravascular (e.g., intravenous), intradermal, intramuscular, or intrathecal injection or infusion techniques and the like. In addition, there is provided a pharmaceutical formulation comprising a compound of the disclosure and a pharmaceutically acceptable carrier. The formulations may be in a form suitable for oral use, for example, as tablets, troches, lozenges, aqueous or oily suspensions, dispersible powders or granules, emulsion, multiple emulsions, hard or soft capsules, or syrups or elixirs.

The magnetically responsive pharmaceutical may be presented in a suitable formulation for an intended delivery route. In some embodiments, the formulation is selected from the group consisting of tablets, gelcaps, softgels, and capsules. The formulations may be made up in a solid form (including granules, powders or suppositories) or in a liquid form (e.g., emulsions). The formulations of the described embodiments may be applied in a variety of solutions and may be subjected to conventional pharmaceutical operations such as sterilization and/or may contain conventional adjuvants, such as preservatives, stabilizers, wetting agents, emulsifiers, buffers, etc.

Pharmaceutical compositions for oral use may contain one or more agents selected from the group consisting of sweetening agents, flavoring agents, coloring agents and preservative agents in order to provide palatable preparations. Tablets contain the formulations in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration, release of drug into surrounding medium and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the MNPs are mixed with an inert solid diluent, for example, calcium carbonate, calcium phosphate or kaolin, in a food product, such as a chocolate, or as soft gelatin capsules wherein the active ingredient is mixed with water or an oil medium, for example peanut oil, liquid paraffin or olive oil.

The magnetically responsive pharmaceutical is then absorbed and distributed over a period of time to at least a target region of the recipient. Absorption and distribution is largely dependent on the route of administration. In one example, the target tissue is adipose tissue in the abdomen of a human recipient and the route of administration for the magnetically responsive pharmaceutical is oral. In this case, the period of time for absorption and distribution includes digestion of the magnetically responsive pharmaceutical and any excipients, travel through the gastrointestinal tract, absorption in the intestines, transfer to the vasculature, and distribution through the blood until the target site is reached.

A magnetic field is then provided to the target region, the magnetic field localizing at least a portion of the magnetically responsive pharmaceutical to the target region, the magnetically responsive pharmaceutical releasing the TRPV1 protein agonist, at 204. The magnetic field may be sourced from either permanent magnets or electromagnets. Further, the magnetic field produced may be continuous or fluctuating. The strength of the magnetic field can vary based on the location of the target site, intervening tissues and other parameters. In one embodiment, a plurality of magnetic fields is used to control the direction and location of the magnetically responsive pharmaceutical. In one example, the magnetic field is between about 0.2 Tesla and about 0.8 Tesla.

The magnetic field may be delivered by a device capable of positioning a magnetic field in proximity of the target region. In one example, the magnetic field is delivered by a permanent magnet, which is positioned in a belt or strap. In another example, a fabric may be interwoven with ferromagnetic threads. The thread in the fabric can either produce a magnetic field or direct a magnetic field from a secondary source, such as an electromagnet connected to the fabric.

The magnetic field may be applied either over the target region, near the target region or in a position to affect the target region based on known physiology. In some embodiments, the magnetic field is applied over the target region. In this case, a stronger magnetic field may be applied such that the magnetically responsive pharmaceutical is held in position at the target region directly by the magnetic field. In another embodiment, the magnetic field is positioned near the target region and downstream of blood flow, thus slowing the migration of the magnetically responsive pharmaceutical near the target region. The magnetic particles can further localize intracellularly and can readily cross the cell membranes, thus allowing for diffusion outside of the vasculature.

The magnetic field can be applied immediately upon administration or after a period of time thereafter. The magnetic field is then maintained until a desired dose of the TRPV1 protein agonist is delivered over a desired period of time in the target region, at 206. The dose delivered relates to the dissolution profile of the magnetically responsive pharmaceutical and the period of time the magnetically responsive pharmaceutical is presented to the target region using the magnetic field. The longer that the magnetic field is maintained, the longer that the magnetically responsive pharmaceutical is in range of the target region.

Figure 3:
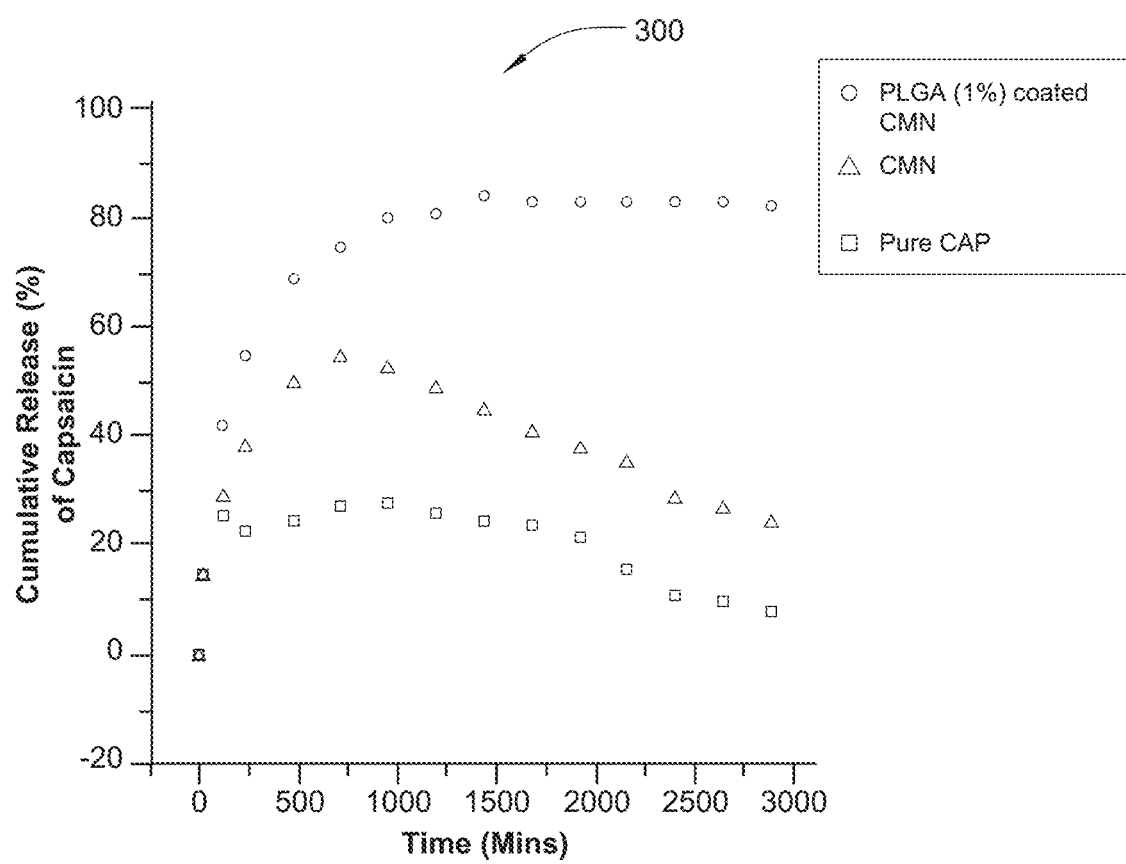
FIG. 3 is a graph depicting cumulative release from magnetically responsive pharmaceuticals prepared according to embodiments described herein.

FIG. 3 is a graph 300 depicting cumulative release from magnetically responsive pharmaceuticals prepared according to embodiments described herein. In this example, ferric chloride (0.6 g, 0.30 mmol) and ferrous chloride (1.4 g, 0.52 mmol) were dissolved in 10 ml of degassed deionized water and ammonium hydroxide (2.4 ml, 29%) was added with fast stirring. The flask was heated to 75° C. for 30 min. and then cooled to 22° C. producing a ferromagnetic fluid. The particles were magnetically filtered and washed with deionized water and neutralized with NaOH. The suspension of the particles in 5 ml of water was heated to 50° C. in a closed vial for 5 min. 1 mM CAP (final concentration of 1 µM) was dissolved in ethanol and diluted with PBS. Final solution of CAP was added drop wise on to the ferromagnetic fluid. PLGA (1.4 gram) dissolved in 5 mL of methylene chloride was added to this mixture with stirring. The aqueous phase was decanted and the PLGA coated capsaicin containing magnetic nanoparticles (CMN) were dried in a vacuum oven. Uncoated CMN were produced by the method above excluding the addition of PLGA. Both the PLGA coated CMN and CMN alone had a 9.29% drug loading efficiency and the PLGA coated CMN had a 89.15% encapsulation efficiency.

CAP release from CMN was monitored for 36 hours in pH 7.4 phosphate buffer at 37° C. in a six channel Vankel dissolution apparatus. Dissolution rate was sustained and prolonged for PLGA (1%) coated CMN compared to uncoated CMN and pure capsaicin. FIG. 3 shows % cumulative CAP releases from 15 minutes to 3000 minutes from pure CAP (squares), CMN (triangles), and PLGA coated CMN (circles). The cumulative release (%) was plotted against time.

$$\text{Cumulative \% Release} = C_1 V_1 \times CF/100 \times C_2$$

$C_1$=Concentration of capsaicin in the final solution (g/ml);
$C_2$=Drug content (mgs) used for dissolution study;
CF=Correction Factor, which is an accommodation for the change in volume due to sampling; and
$V_1$=Volume of dissolution medium (ml)

Both the pure CAP and the CMN show peak CAP concentrations at around 500 minutes and the concentrations then steadily decrease as both samples approach 3000 minutes. The PLGA coated CMN shows a sustained release, peaking at about 1000 minutes and continuing beyond 300 minutes at approximately the same level. The graph 300 shows that the CMN, both with and without the PLGA coating delivers a sustained and steady concentration of CAP.

Figure 4:
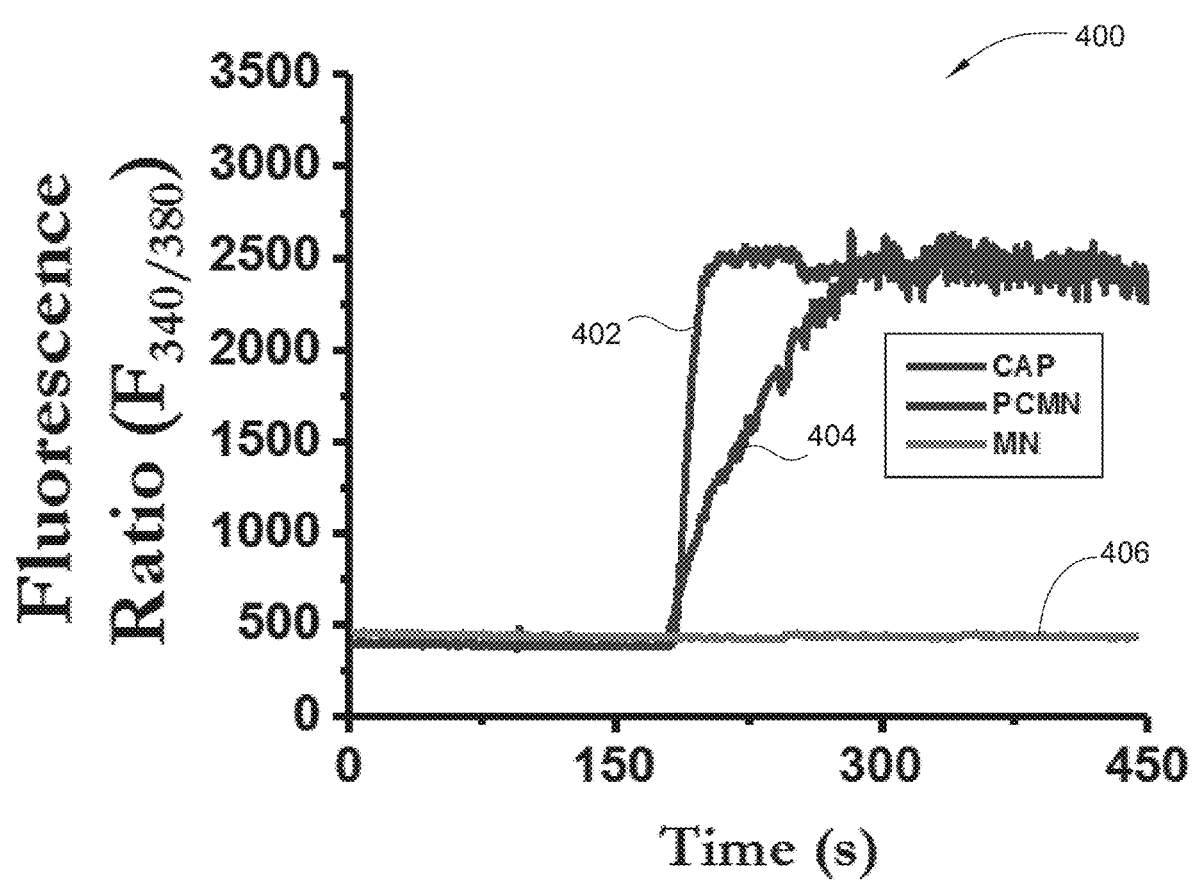
FIG. 4 is a graph of the time to peak rise of $Ca^{2+}$ for poly(lactide-co-glycolide) (PLGA) coated capsaicin containing magnetic nanoparticles (CMN), pure capsaicin (CAP) and MNPs containing no CAP, according to embodiments described herein.

FIG. 4 is a graph 400 of the time to peak rise of $Ca^{2+}$ for PLGA coated CMN, pure CAP and MNPs containing no CAP, according to embodiments described herein. HEK293 cells expressing TRPV1 channel protein (CAP receptor) grown on coverslips were loaded with Fura-2 AM (2 µM) for 40 minutes at room temperature. Cells were washed and then viewed with a Leica DMI3000 B inverted microscope coupled to a Polychrome V digital imaging system with Imago CCD camera. Cells were continuously superfused (22 degrees Celsius) with 2 mM $Ca^{2+}$ containing normal extracellular solution (NES). The $Ca^{2+}$ influx due to the addition of pure capsaicin (1 µM), CMN or PCMN (equivalent of 1 µM CAP), was observed and measured as a function of fluorescence.

The time to peak rise of $Ca^{2+}$ is lower for PLGA coated CMN compared to pure CAP. The time course of MNPs (at element 406), pure CAP (at element 404) and PLGA coated CMN (at element 402) stimulated intracellular $Ca^{2+}$ rise in TRPV1 expressing HEK293 cells is plotted on the graph 400. The rise in $Ca^{2+}$ concentration in both the PLGA coated CMN sample and the pure CAP sample begins at approximately 175 seconds. However, the PLGA coated CMN sample achieves a peak rise in $Ca^{2+}$ concentration at about 175 seconds while the pure CAP sample achieves a peak rise in $Ca^{2+}$ concentration at about 300 seconds. The MNPs sample (control) shows no rise in $Ca^{2+}$ concentration over the time course of 450 seconds.

Thus, the PLGA coated CMN is capable of agonizing the TRPV1 receptor and the response is not related to the magnetic particle (as shown by no response from the control). These results suggest that PLGA coating and/or the MNPs do not interfere with the pharmacological effects of CAP. Surprisingly, the response elicited in the PLGA coated CMN sample was stronger than pure CAP at the same approximate CAP concentration (1 µM).

Described herein are magnetically responsive pharmaceuticals for use in targeted anti-obesity treatment, methods of making said pharmaceuticals and methods of using the same. The pharmaceuticals and methods described herein target a TRPV1 protein agonist to a specific site in the body. Through this pathway, pharmaceuticals and methods described herein can inhibiting weight gain, decrease fat deposition/oil droplet accumulation in adipocytes, stimulate metabolic activity, increase transcription factors that regulate adipogenesis and brown fat thermogenesis, trigger the molecular switch for brown in white cell transition (i.e., formation of "Brite" cells), increase thermogenic genes in brown fat tissue and increase the genes/proteins that stabilize transcriptional factors that regulate adipogenesis.

While the foregoing is directed to embodiments of the present disclosure, other and further embodiments of the disclosure may be devised without departing from the basic scope thereof, and the scope thereof is determined by the claims that follow.

What is claimed is:

1. A method for making a magnetically responsive pharmaceutical, comprising:
   forming magnetic nanoparticles (MNPs), comprising:
      precipitating ferromagnetic materials in the presence of ammonium hydroxide to obtain a mixture comprising MNPs; and
      adding a TRPV1 protein agonist to the mixture; and
      coating the mixture with a biodegradable polymer.

2. The method of claim 1, further comprising:
   dissolving the coated MNPs in a chlorinated solvent; and
   evaporating the coated MNPs.

3. The method of claim 1, further comprising:
   prior to coating the MNPs, decanting the mixture; and
   drying the MNPs in a vacuum oven.

4. The method of claim 1, wherein the ferromagnetic materials are selected from the group consisting of iron, iron oxide, cobalt, cobalt oxide, nickel, nickel oxide, and combinations thereof.

5. The method of claim 1, wherein the ferromagnetic materials comprise metal salts selected from the group consisting of iron-based salts, nickel-based salts, cobalt-based salts, and combinations thereof.

6. The method of claim 5, wherein the metal salts are selected from the group consisting of iron (II) sulfate, iron (II) nitrate, iron (II) chloride, iron (II) perchlorate, iron (III) sulfate, iron (III) nitrate, iron (III) chloride, iron (III) perchlorate, and combinations thereof.

7. The method of claim 1, wherein the TRPV1 agonist is selected from the group consisting of dihydrocapsiate, capsaicin, civamide, vanillin, endovanilloids, resiniferatoxin, N-VanillyInonanamide, capsiate, Capsaicin β-D-Glucopyranoside, and combinations thereof.

8. The method of claim 7, wherein the TRPV1 agonist is capsaicin.

9. The method of claim 1, wherein the biodegradable polymer is selected from the group consisting of poly(lactic-co-glycolic acid) (PLGA), Polylactic acid (PLA), Polyglycolic acid (PGA), poly-D-lactic acid (PDLA), PLGA-dimethacrylate, fluorescent PLGA polymers, Poly(ethyl acrylate-co-methyl methacrylate-co-trimethylammonioethyl methacrylate chloride) 1:2:0.2, Poly(ethyl acrylate-co-methyl methacrylate-co-trimethylammonioethyl methacrylate chloride) 1:2:0.1, Ethyl cellulose, and combinations thereof.

10. The method of claim 9, wherein the biodegradable polymer is poly(lactic-co-glycolic acid) (PLGA).

11. A method for making a magnetically responsive pharmaceutical, comprising:
    precipitating ferromagnetic metal salts in the presence of ammonium hydroxide to obtain magnetic nanoparticles (MNPs);
    depositing a TRPV1 protein agonist in the MNPs; and
    coating the MNPs and the TRPV1 protein agonist with a biodegradable polymer.

12. The method of claim 11, wherein the ferromagnetic metal salts are selected from the group consisting of iron, cobalt, nickel, and combinations thereof.

13. The method of claim 12, wherein the ferromagnetic metal salts are selected from the group consisting of iron (II) sulfate, iron (II) nitrate, iron (II) chloride, iron (II) perchlorate, iron (III) sulfate, iron (III) nitrate, iron (III) chloride, iron (III) perchlorate, and combinations thereof.

14. The method of claim 11, wherein the TRPV1 agonist is selected from the group consisting of dihydrocapsiate, capsaicin, civamide, vanillin, endovanilloids, resiniferatoxin, N-VanillyInonanamide, capsiate, Capsaicin β-D-Glucopyranoside, and combinations thereof.

15. The method of claim 11, wherein the biodegradable polymer is selected from the group consisting of poly(lactic-co-glycolic acid) (PLGA), Polylactic acid (PLA), Polyglycolic acid (PGA), poly-D-lactic acid (PDLA), PLGA-dimethacrylate, fluorescent PLGA polymers, Poly(ethyl acrylate-co-methyl methacrylate-co-trimethylammonioethyl methacrylate chloride) 1:2:0.2, Poly(ethyl acrylate-co-methyl methacrylate-co-trimethylammonioethyl methacrylate chloride) 1:2:0.1, Ethyl cellulose, cellulose derivatives, and combinations thereof.

16. The method of claim 11, wherein the MNPs comprises metal ions, and wherein a molar ratio of biodegradable polymer to metal ions is between about 1:40 and about 1:300.

17. The method of claim 1, wherein the MNPs comprise $Fe^{3+}$ and $Fe^{2+}$ ions in a molar ratio of between about 3:1 and about 1:1 $Fe^{3+}$ to $Fe^{2+}$ ions.

18. The method of claim 11, wherein the MNPs comprises metal ions, and wherein a molar ratio of biodegradable polymer to metal ions is between about 1:40 and about 1:300.

19. The method of claim 11, wherein the MNPs are between about 5 nm and about 30 nm in diameter.

20. A method for making a magnetically responsive pharmaceutical, comprising:
   precipitating magnetic nanoparticles (MNPs) by a heating a mixture of ferromagnetic metal salts in the presence of a TRPV1 agonist and ammonium hydroxide temperature above 60 degrees Celsius followed by cooling to a temperature at or below room temperature; and
   coating the MNPs and the TRPV1 protein agonist with a biodegradable polymer.

* * * * *